US00PP11929P2

(12) United States Plant Patent
Huber

(10) Patent No.: US PP11,929 P2
(45) Date of Patent: Jun. 19, 2001

(54) RUDBECKIA PLANT NAMED 'POT OF GOLD'

(75) Inventor: Tony Huber, Laval (CA)

(73) Assignee: Norseco Inc., Laval (CA)

( * ) Notice: Subject to any disclaimer, the term of this patent is extended or adjusted under 35 U.S.C. 154(b) by 0 days.

(21) Appl. No.: 09/292,197

(22) Filed: Apr. 15, 1999

(51) Int. Cl.[7] ..... A01H 5/00
(52) U.S. Cl. ..... Plt./263
(58) Field of Search ..... Plt./263

(56) References Cited

U.S. PATENT DOCUMENTS

P.P. 8,867 * 8/1994 Viette ..... Plt./263

* cited by examiner

*Primary Examiner*—Bruce R. Campell
*Assistant Examiner*—Wendy A Baker
(74) *Attorney, Agent, or Firm*—C. A. Whealy

(57) ABSTRACT

A distinct cultivar of Rudbeckia plant named 'Pot of Gold', characterized by its compact, uniform and mounded plant habit; freely branching and vigorous; large leaves; large inflorescences with intense golden yellow ray florets and dark brown disc florets; and good garden performance and very good resistance to drought conditions.

3 Drawing Sheets

BACKGROUND OF THE INVENTION

The present invention relates to a new and distinct cultivar of Rudbeckia plant, botanically known as *Rudbeckia fulgida* var. Sullivantii and referred to by the cultivar name Pot of Gold.

The new cultivar is a product of a planned breeding program conducted by the Inventor in Boisbriand, Quebec, Canada. The objective of the breeding program was to create new compact Rudbeckia cultivars with uniform plant habit, large inflorescences and intense ray floret color.

The new cultivar originated from a self-pollination made by the Inventor of the *Rudbeckia fulgida* var. Sullivantii cultivar Goldstrum, not patented. The new Rudbeckia was selected by the Inventor as a flowering plant within the progeny of this cross in a controlled environment in Boisbriand, Quebec, Canada, in the 1990.

Plants of the new cultivar are different from plants of the parent, the cultivar Goldstrum, in the following characteristics:

1. Plants of the new Rudbeckia are more compact than plants of the cultivar Goldstrum.

2. Plants of the new Rudbeckia are more uniform in plant habit and height than plants of the cultivar Goldstrum.

3. Plants of the new Rudbeckia have larger inflorescences than plants of the cultivar Goldstrum.

4. Ray floret color of the new Rudbeckia is much more intense than ray floret color of the cultivar Goldstrum.

Asexual propagation of the new cultivar by crown divisions and by terminal cuttings at Boisbriand, Quebec, Canada, has shown that the unique features of this new Rudbeckia are stable and reproduced true to type in successive generations.

SUMMARY OF THE INVENTION

The following traits have been repeatedly observed and are determined to be the unique characteristics of 'Pot of Gold'. These characteristics in combination distinguish 'Pot of Gold' as a new and distinct cultivar:

1. Compact, uniform and mounded plant habit.

2. Freely branching and vigorous.

3. Large leaves.

4. Large inflorescences with intense golden yellow ray florets and dark brown disc florets.

5. Good garden performance and very good resistance to drought conditions.

The cultivar Pot of Gold has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a top perspective view of typical rows of flowering plants of 'Pot of Gold'.

The photograph on the second sheet comprises a top perspective view of typical plants of 'Pot of Gold'.

The photograph on the third page comprises a close-up view of typical inflorescences of 'Pot of Gold'. Foliage and floret colors in the photographs may appear different from the actual colors due to light reflectance.

DETAILED BOTANICAL DESCRIPTION

The following observations, measurements and values describe plants of the new cultivar grown in ground beds north of Montreal, Quebec, Canada, under outdoor, full-sun conditions.

Color references are made to The Royal Horticultural Society Colour Chart except where general terms of ordinary dictionary significance are used.

Botanical classification: *Rudbeckia fulgida* var. Sullivantii cultivar Pot of Gold.

Parentage: Self-pollination of *Rudbeckia fulgida* var. Sullivantii cultivar Goldstrum, not patented.

Propagation:

*Type.*—By crown divisions or by terminal cuttings.

*Time to initiate roots, April.*—About 20 days at 18° C.

*Time to develop roots, April.*—About 40 days at 18° C.

*Root description.*—Fine.

Plant description:

*Appearance.*—Perennial herbaceous container and garden plant. Compact, erect and upright, bushy and mounded growth habit. Freely branching with about four lateral branches from main stem.

*Crop time.*—From planting rooted cuttings, about 8 to 12 weeks are required to produce a finished plant. From planting a division, about 4 to 6 weeks are required to produce a finished plant. Plants are typically planted on 9-cm squares or in one-liter containers.

*Growth rate.*—Rapid.

*Plant height.*—About 60 cm.

*Plant spread.*—About 60 cm.

*Lateral branch description.*—Length: About 16.7 cm. Diameter: About 2.8 mm. Internode length: About 3.8 mm. Texture: Slightly pubescent; six-sided, fluted stems. Color: 143B; at the end of the summer, stems become covered with longitudinal burgundy red streaks.

*Foliage description.*—Leaves alternate, single; very durable. Length, fully expanded leaves, basal: About 13 cm. Width, fully expanded leaves, basal: About 7.5 cm. Shape: Elliptic to ovate. Apex: Acuminate to acute. Base: Basal leaves, obtuse to cuneate; upper leaves, cuneate to attenuate. Margin: Entire, serrate or crenate. Texture: Rough; slight to moderate pubescence on both surfaces. Petioles: Basal leaves with long petioles; petiole length less with distal leaves; uppermost leaves, bract-like. Color: Immature leaves, upper surface: Typically 136A, some leaves lighter than 139A and some darker than 137A. Immature leaves, lower surface: 147B. Mature leaves, upper surface: 139A. Mature leaves, lower surface: 137C. Venation, upper surface: 143C. Venation, lower surface: 147C. Petiole: 147B.

Inflorescence description:

*Appearance.*—Daisy-type composite inflorescence form. Disc and ray florets arranged acropetally on a capitulum. Inflorescences displayed above and beyond foliage; one inflorescence per lateral stem; peduncles arising from leaf axils. Inflorescences last about 8 to 10 days. Ray florets, self cleaning; disc florets, persistent.

*Flowering response.*—Plants flower continuously from July to October in Quebec, Canada.

*Fragrance.*—Faint, not very pleasant.

*Quantity of inflorescences.*—About 105 per plant.

*Inflorescence buds.*—Length: About 9 mm. Diameter: About 1.3 cm. Shape: Flattened sphere. Rate of opening: About 15 days. Color: Light green, in between 144A and 144B.

*Inflorescence longevity.*—About 9 days.

*Inflorescense size.*—Diameter: About 10 cm. Depth (height): About 1.3 to 1.5 cm.

*Ray florets.*—Length: About 4 cm. Width: About 1 to 1.5 cm. Shape: Ligulate, elongated. Apex: Bifid, acute. Base: Obtuse. Margin: Entire. Aspect: Flat to recurved. Texture: Smooth, satiny. Number of ray florets per inflorescence: About 14 in a single whorl. Color: When opening, upper surface: 17C. When opening, lower surface: No match to R.H.S. Colour Chart, close to a mixture of 149A and 12A. Fully opened, upper surface: 17A; color does not fade. Fully opened, lower surface: More dull than upper surface, close to 14A.

*Disc florets.*—Shape: Tubular. Number of disc florets per inflorescence: Numerous, about 225 to 350. Length: About 3 to 6 mm. Width: About 1 mm. Color: Immature: 200A. Mature: 200A.

*Phyllaries.*—Length: About 3.2 cm. Diameter of whorl: About 1.5 cm. Shape: Linear. Apex: Pointed. Margin: Entire. Quantity and arrangement: About 16 per inflorescence; whorled, two rows. Texture: Stiff, prickly. Color: Outer surface: Apex, 139A; mid-section, between 141A and 141B; base, between 143B and 143C. Inside surface: Apex, 139A; mid-section, between 141B and 141C; base, between 143B and 143C.

*Peduncle.*—Length: Terminal peduncle: About 20 cm. Fourth peduncle: About 10 cm. Aspect: Rigid, straight, strong; inflorescences held above foliage. Texture: Rugose. Color: 143B.

*Reproductive organs.*—Androecium: Present on disc florets only. Stamens: Four or five; fused. Anther length: About 3.5 mm. Anther color: Deep maroon. Pollen amount: Scarce. Pollen color: 23A. Gynoecium: Present on ray and disc florets. Pistils: One. Pistil length: About 4 mm. Stigma shape: Long and narrow. Stigma color: Deep maroon. Style length: About 2 mm. Style color: Deep maroon. Ovary color: Light greenish purple. Seed: Length: About 3 mm. Diameter: About 1 mm. Color: No match to R.H.S. Colour Chart, but deeper than 197A.

Disease resistance: The new Rudbeckia has exhibited good resistance to pathogens common to Rudbeckia.

Garden performance: Plants of the new Rudbeckia have demonstrated good garden performance and very good resistance to drought conditions.

It is claimed:

1. A new and distinct cultivar of Rudbeckia plant named 'Pot of Gold', as illustrated and described.

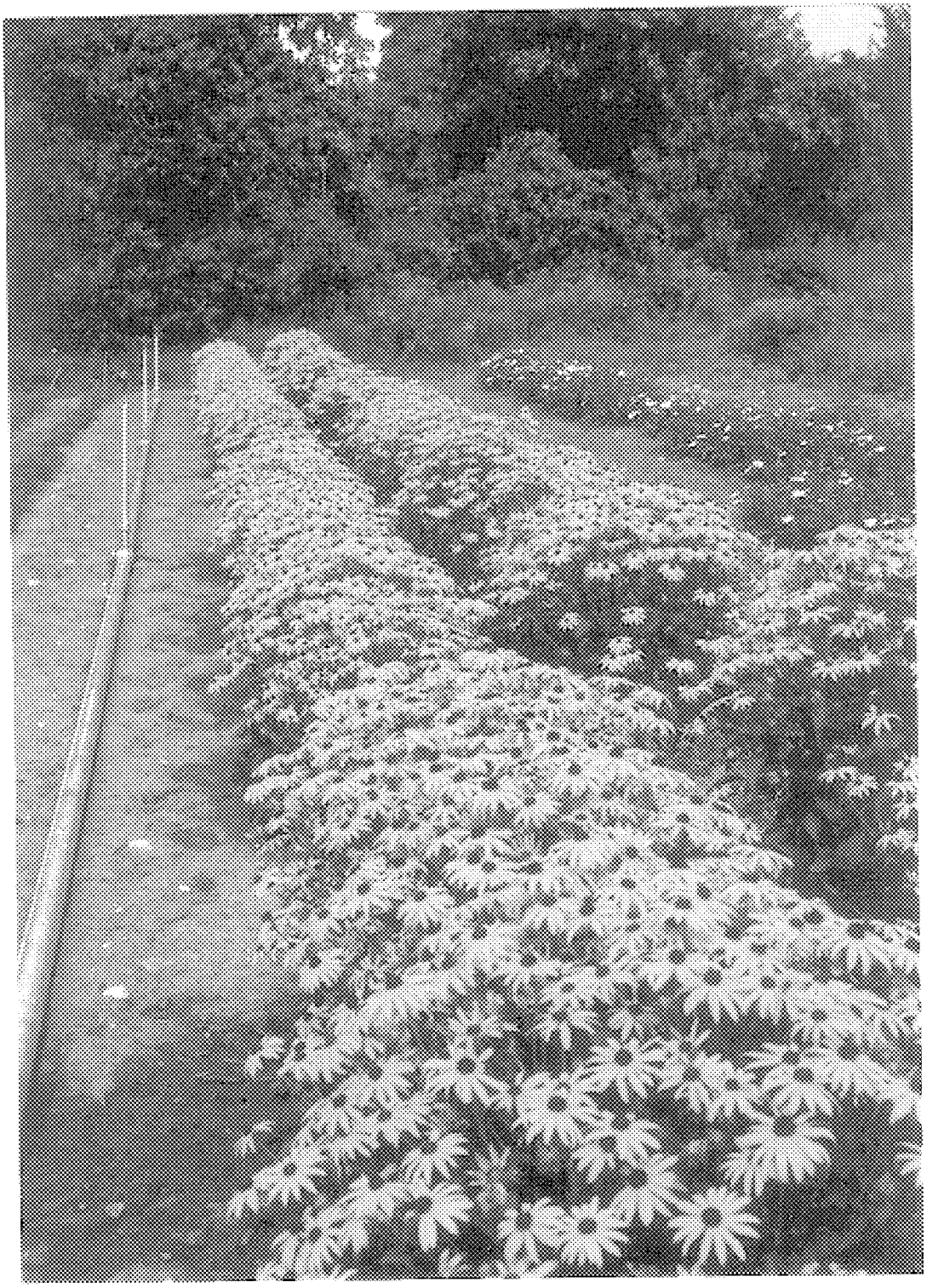

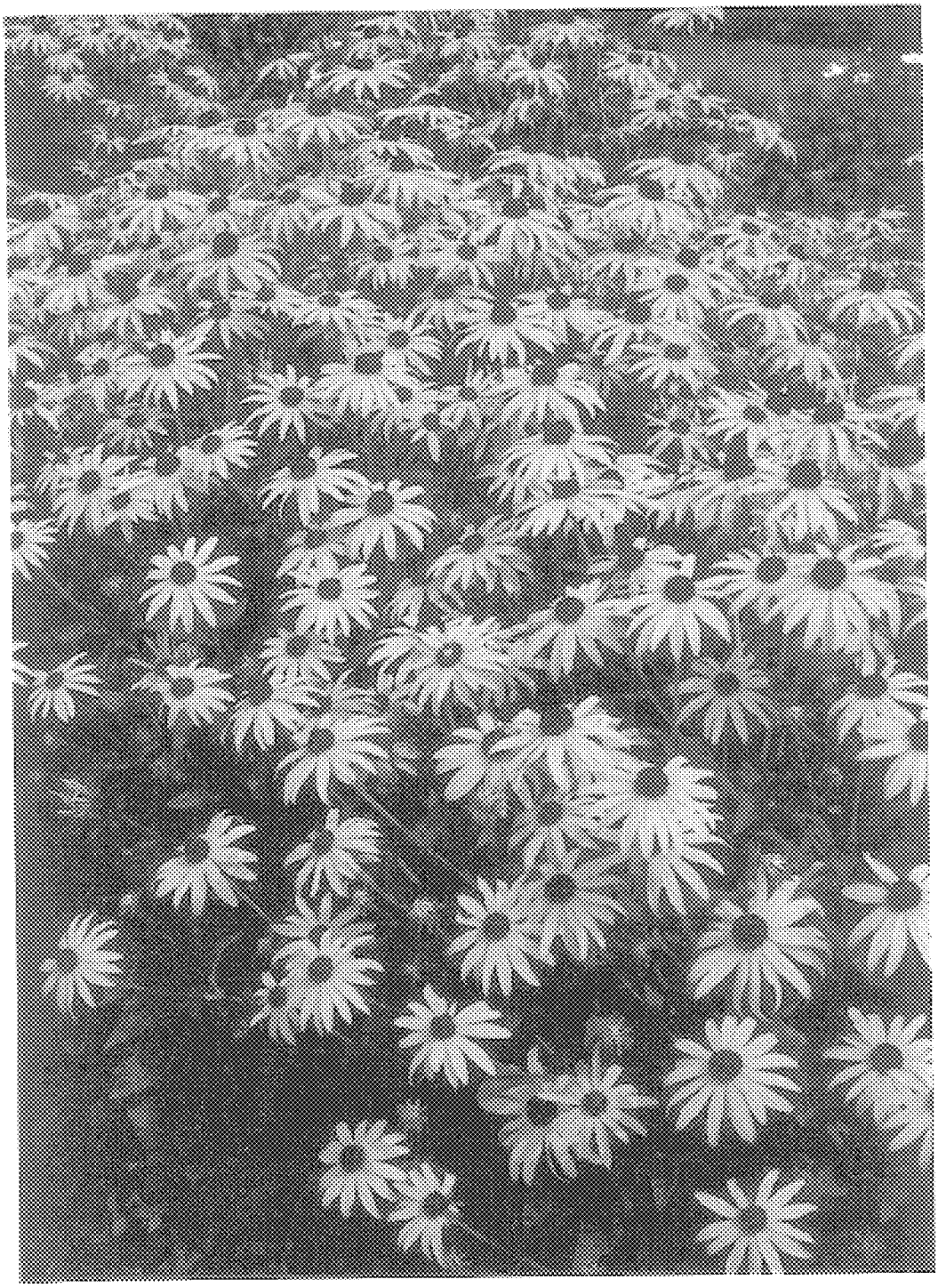

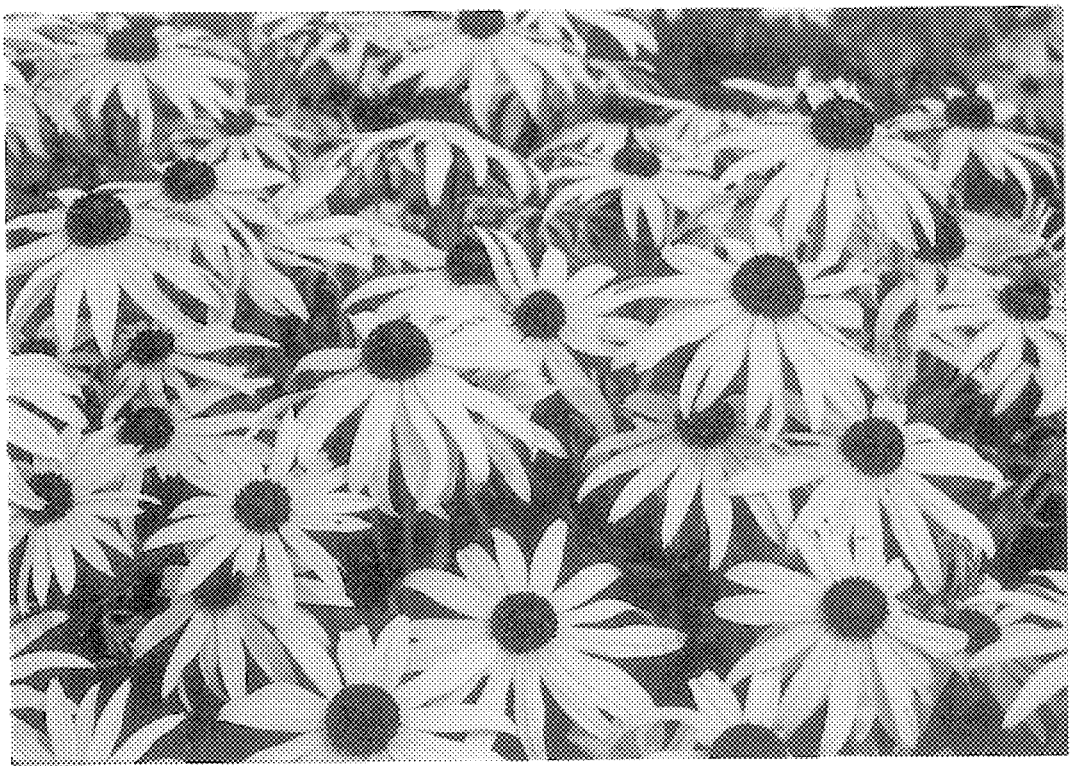

* * * * *